United States Patent
Frewin et al.

(10) Patent No.: US 8,751,015 B2
(45) Date of Patent: Jun. 10, 2014

(54) GRAPHENE ELECTRODES ON A PLANAR CUBIC SILICON CARBIDE (3C-SIC) LONG TERM IMPLANTABLE NEURONAL PROSTHETIC DEVICE

(71) Applicants: Christopher Leroy Frewin, Tampa, FL (US); Stephen E. Saddow, Odessa, FL (US); Camilla Coletti, Pisa (IT)

(72) Inventors: Christopher Leroy Frewin, Tampa, FL (US); Stephen E. Saddow, Odessa, FL (US); Camilla Coletti, Pisa (IT)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 13/905,909

(22) Filed: May 30, 2013

(65) Prior Publication Data
US 2013/0338744 A1    Dec. 19, 2013

Related U.S. Application Data

(63) Continuation of application No. PCT/US2011/062601, filed on Nov. 30, 2011.

(60) Provisional application No. 61/418,200, filed on Nov. 30, 2010.

(51) Int. Cl.
*A61N 1/00* (2006.01)

(52) U.S. Cl.
USPC .................................................. 607/116

(58) Field of Classification Search
USPC .................................................. 607/116
See application file for complete search history.

(56) References Cited

U.S. PATENT DOCUMENTS

| | | | |
|---|---|---|---|
| 3,057,356 A | 10/1962 | Greatbatch | |
| 4,461,304 A | 7/1984 | Kuperstein | |
| 5,855,801 A | 1/1999 | Lin et al. | |
| 6,480,743 B1 | 11/2002 | Kirkpatrick et al. | |
| 6,829,498 B2 | 12/2004 | Kipke et al. | |
| 6,952,687 B2 | 10/2005 | Andersen et al. | |
| 6,993,392 B2 | 1/2006 | Nicolelis et al. | |
| 7,015,142 B2 | 3/2006 | DeHeer et al. | |
| 7,107,104 B2 | 9/2006 | Keravel et al. | |

(Continued)

FOREIGN PATENT DOCUMENTS

| | | |
|---|---|---|
| WO | 0172201 A1 | 10/2001 |
| WO | 2009012502 A1 | 1/2009 |

OTHER PUBLICATIONS

K. Geim and K. S. Novoselov, "The rise of graphene," Nature Materials, Mar. 2007. vol. 6:183-191.

(Continued)

*Primary Examiner* — Robert N Wieland
(74) *Attorney, Agent, or Firm* — Michele L. Lawson; Smith & Hopen, P.A.

(57) ABSTRACT

Graphene, can be used to make an implantable neuronal prosthetic which can be indefinitely implanted in vivo. Graphene electrodes are placed on a 3C—SiC shank and electrical insulation is provided by conformal insulating SiC. These materials are not only chemically resilient, physically durable, and have excellent electrical properties, but have demonstrated a very high degree of biocompatibility. Graphene also has a large specific capacitance in electrolytic solutions as well as a large surface area which reduces the chances for irreversible Faradaic reactions. Graphene can easily be constructed on SiC by the evaporation of Si from the surface of that material allowing for mechanically robust epitaxial graphene layers that can be fashioned into electrodes using standard lithography and etching methods.

19 Claims, 10 Drawing Sheets

(56) References Cited

U.S. PATENT DOCUMENTS

| | | | |
|---|---|---|---|
| 7,120,486 | B2 | 10/2006 | Leuthardt et al. |
| 7,548,775 | B2 | 6/2009 | Kipke et al. |
| 2006/0134096 | A1 | 6/2006 | Petrik |
| 2006/0293578 | A1 | 12/2006 | Rennaker, II |
| 2007/0060815 | A1 | 3/2007 | Martin et al. |
| 2007/0293910 | A1 | 12/2007 | Strother et al. |
| 2009/0020764 | A1 | 1/2009 | Anderson et al. |
| 2009/0169919 | A1 | 7/2009 | Garcia et al. |
| 2009/0181502 | A1* | 7/2009 | Parikh et al. .......... 438/164 |
| 2009/0248113 | A1 | 10/2009 | Nimer et al. |
| 2012/0028052 | A1* | 2/2012 | Chu et al. ............ 428/428 |
| 2012/0232631 | A1 | 9/2012 | Frewin et al. |
| 2013/0090542 | A1* | 4/2013 | Kipke et al. .......... 600/377 |

OTHER PUBLICATIONS

S. Harrison and A. Atala, "Carbon nanotube applications for tissue engineering," Biomaterials, 2007. vol. 28:344-353.

Berger, et al., "Ultrathin epitaxial graphite: 2D electron gas properties and a route toward graphene-based nanoelectronics," Journal of Physical Chemistry B. 2004. vol. 108:19912-19916.

Riedl, et al., "Quasi-Free-Standing Epitaxial Graphene on SiC Obtained by Hydrogen Intercalation," Physical Review Letters, 2009. vol. 103:1-4.

C. Virojanadara, et al., "Buffer layer free large area bi-layer graphene on SiC(0001)," Surface Science, 2010. vol. 604: L4-L7.

R. Merrill, et al., "Electrical stimulation of excitable tissue: design of efficacious and safe protocols," Journal of Neuroscience Methods, 2005. vol. 141: 171-198.

Jan and N. A. Kotov, "Successful differentiation of mouse neural stem cells on layer-by-layer assembled single-walled carbon nanotube composite," Nano Letters, 2007. vol. 7 (No. 5):1123-1128.

E. R. Edelman and C. Rogers, "Stent-versus-stent equivalency trials—Are some stents more equal than others?," Circulation, 1999. vol. 100: 896-898.

S. Wilson and R. Gifford, "Biosensors for real-time in vivo measurements," Biosensors & Bioelectronics, 2005. vol. 20:2388-2403.

Chen, et al., "Mechanically strong, electrically conductive, and biocompatible graphene paper," Advanced Materials, 2008. vol. 20:3557-3561.

W. Frank, et al., "Mechanical properties of suspended graphene sheets," Journal of Vacuum Science & Technology B, 2007. vol. 25:2558-2561.

Willner and B. Willner, "Biomaterials integrated with electronic elements: en route to bioelectronics," Trends in Biotechnology, 2001. vol. 19:222-230.

A. Porter and J. A. Von Fraunhofer, "Success or failure of dental implants? A literature review with treatment considerations," Gen Dent, Nov.-Dec. 2005. vol. 53:423-32; quiz 433.

J. Hass, et al., "The growth and morphology of epitaxial multilayer graphene," Journal of Physics-Condensed Matter, 2008. vol. 20:323202(1-27).

J. Kedzierski, et al., "Epitaxial graphene transistors on SIC substrates," Ieee Transactions on Electron Devices, 2008. vol. 55:2078-2085.

J. S. Moon, et al., "Epitaxial-Graphene RF Field-Effect Transistors on Si-Face 6H-SiC Substrates," IEEE Electron Device Letters. 2009. vol. 30:650-652.

S. Kim, et al., "Large-scale pattern growth of graphene films for stretchable transparent electrodes," Nature, 2009. vol. 457: 706-710.

K. S. Novoselov, et al., "Electric field effect in atomically thin carbon films," Science, 2004. vol. 306: 666-669.

L. Hench and J. Wilson, "Biocompatibility of Silicates for Medical Use," Ciba Foundation Symposia, 1986. vol. 121:231-246.

D. Stoller, et al., "Graphene-Based Ultracapacitors," Nano Letters, 2008. vol. 8 (Issue 10):3498-3502.

M. Pumera, "Electrochemistry of Graphene: New Horizons for Sensing and Energy Storage," Chemical Record, 2009. vol. 9:211-223.

M.Y. Han, et al., "Energy band-gap engineering of graphene nanoribbons," Physical Review Letters, 2007. vol. 98:1-4.

P. Guisinger, et al., "Atomic-scale investigation of graphene formation on 6H-SiC(0001)," Journal of Vacuum Science & Technology A, Jul.-Aug. 2008. vol. 26:932-937.

G. Whitten, et al., "Free standing carbon nanotube composite bioelectrodes," Journal of Biomedical Materials Research Part B—Applied Biomaterials, Jul. 2007. vol. 82B:37-43.

Sutter, "Epitaxial graphene How silicon leaves the scene," Nature Materials, 2009. vol. 8:171-172.

P. W. Sutter, et al. , "Epitaxial graphene on ruthenium," Nature Materials, 2008. vol. 7:406-411.

Agarwal, et al., "Interfacing Live Cells with Nanocarbon Substrates," Langmuir, 2010. vol. 26 (No. 4): 2244-2247.

F. Cogan, "Neural stimulation and recording electrodes," Annu Rev Biomed Eng, 2008. vol. 10:275-309.

P. Pang, et al., "Patterned Graphene Electrodes from Solution-Processed Graphite Oxide Films for Organic Field-Effect Transistors," Advanced Materials, 2009. vol. 21:3488-3491.

S. R. C. Vivekchand, et al., "Graphene-based electrochemical supercapacitors," Journal of Chemical Sciences, 2008. vol. 120:9-13.

S. Y. Zhou, et al., "Substrate-induced bandgap opening in epitaxial graphene," Nature Materials, 2007. vol. 6:770-775.

T T. Ohta, et al., "Controlling the electronic structure of bilayer graphene," Science, 2006. vol. 313: 951-954.

Lovat, et al., "Carbon nanotube substrates boost neuronal electrical signaling," Nano Letters, 2005. vol. 5 (No. 6)1107-1110.

Y. Aristov, et al., "Graphene Synthesis on Cubic SiC/Si Wafers. Perspectives for Mass Production of Graphene-Based Electronic Devices," Nano Letters, 2010. vol. 10:992-995.

Greatbatch, "Implantable Cardiac Pacemakers," Proceedings of the Institute of Radio Engineers, 1960. vol. 48:386-386.

M. Chardack, et al., "Experimental observations and clinical experiences with the correction of complete heart block by an implantable, self-contained pacemaker," American Society for Artificial Internal Organs, 1961. vol. 7 (Issue 1):286-294.

W. R. Yang, et al., "Carbon Nanomaterials in Biosensors: Should You Use Nanotubes or Graphene?," Angewandte Chemie-International Edition, 2010. vol. 49:2114-2138.

Wang, et al., "Transparent, conductive graphene electrodes for dye-sensitized solar cells," Nano Letters, 2008. vol. 8:323-327.

Wang, et al., "Application of graphene-modified electrode for selective detection of dopamine," Electrochemistry Communications, 2009. vol. 11:889-892.

J. J. Jacobs et al., "Corrosion of metal orthopaedic implants," J Bone Joint Surg Am, 1998. vol. 80 (No. 2 ):268-82.

P. J. Rousche, R. A. Normann, "Chronic recording capability of the Utah Intracortical Electrode Array in cat sensory cortex" Journal of Neuroscience Methods. 1998. vol. 82:1-15.

J. A. Hosp et al., "Thin-film epidural microelectrode arrays for somatosensory and motor cortex mapping in rat", Journal of Neuroscience Methods, 2008. vol. 172:255-262.

J. W. Fawcett and R. A. Asher, "The glial scar and central nervous system repair", Brain Research Bulletin, 1999. vol. 49 (No. 6):377-391.

K. Lee et al., "Biocompatible benzocyclobutene-based intracortical neural implant with surface modification", J. Micromech. Microeng. 2005. vol. 15:2149-2155.

D. R. Kipke et al., "Advanced neural implants using thin-film polymers", ISCAS. 2002. vol. 4:173-176.

P. J. Rousche et al., "Flexible polyimide-based intracortical electrode arrays with bioactive capability," IEEE Trans. Biomed. Eng., 2001. vol. 48 (No. 3):361-371.

J. Vidal, "Toward direct brain-computer communication", in Annual Review of Biophysics and Bioengineering, L. J. Mullins, Ed. Palo Alto, CA, USA: Annual Reviews, Inc., 1973, vol. 2:157-180.

K. D. Wise et al., "Microelectrodes, microelectronics, and implantable neural microsystems", Proceedings of the IEEE, 2008. vol. 96 (No. 7):1184-1202.

M. A. Lebedev, and M. A. L. Nicolelis, "Brain-machine interfaces: past, present and future", Trends Neurosci., 2006. vol. 29 (No. 9):536-546.

N. C. Berchtold, C. W. Cotman, "Evolution in the conceptualization of dementia and Alzheimer's disease: Greco-Roman period to the 1960s". Neurobiol. Aging. 1998. vol. 19 (No. 3):173-89.

(56) References Cited

OTHER PUBLICATIONS

J. Jankovic, "Parkinson's disease: clinical features and diagnosis". J. Neurol. Neurosurg. Psychiatr. 2008. vol. 79 (No. 4): 368-376.

C. Richards-Grayson, R. S. SHAWGO, and A. M. Johnson, "A bioMEMS review: MEMS technology for physiologically integrated devices", Proceedings of the IEEE, 2004. vol. 92 (No. 1):6-21.

J. K. Chapin et al., "Real-time control of a robot arm using simultaneously recorded neurons in the motor cortex", Nature Neuroscience, 1999. vol. 2 (No. 7):pp. 664-670.

M. Santos, J. R. Fernandes, and M. S. Pieda, "A Microelectrode Stimulation System for a Cortical Neuroprosthesis", Conference on Design of Circuits and Integrated Systems, Barcelona, Spain, 2006.

C. E. Schmidt and J. B. Leach, "Neural Tissue Engineering: Strategies for Repair and Regeneration", Annu. Rev. Biomed. Eng., 2003. vol. 5:293-347.

S. Martinoia et al., "Cultured neurons coupled to microelectrode arrays: circuit models, simulations and experimental data", IEEE Transactions on Biomedical Engineering, 2004. vol. 51 (No. 5): 859-864.

Kennedy, P. R., and Bakay, R. A. E., "Restoration of neural output from a paralyzed patient by a direct brain connection", NeuroReport 1998. vol. 9:1707-1711.

L. Hodgkin and A. F. Huxley, "Currents carried by sodium and potassium ions through the membrane of the giant axon of Loligo", J. Physiol. (Lond.), 1952. vol. 116 (No. 4):449-472.

L. Hodgkin and A. F. Huxley, "The dual effect of membrane potential on sodium conductance in the giant axon of Loligo", J. Physiol (Lond.), 1952. vol. 116 (No. 4):497-506.

L. Hodgkin and A. F. Huxley, "A quantitative description of membrane current and its application to conduction and excitation in nerve", J. Physiol (Lond.), 1952. vol. 117 (No. 4):500-544.

Guld, "A glass-covered platinuim microelectrode," Med. Electron. Biol. Engng. 1964. vol. 2:317-327.

K. D. Wise et al., "An Integrated-Circuit Approach to Extracellular Microelectrodes", IEEE Transactions on Bio-medical engineering, 1970. vol. BME-17 (No. 3):238-247.

M. Kuperstein, and D. Whittington, "A Practical 24 Channel Microelectrode for Neural Recording in Vivo", IEEE Transactions on Bio-medical engineering. 1981. vol. BME-28 (No. 3):288-293.

K. L. Drake et al., "Performance of Planar Multisite Microprobes in Recording Extracellular Single-Unit Intracortical Activity", IEEE Transactions on Bio-medical engineering, 1988. vol. BME-35 (No. 9):719-732.

R. Kipke, "Implantable neural probe systems for cortical neuroprostheses," Dig. IEEE Conf. Eng. Med. Biol., San Francisco, CA, Sep. 2004:5344-5347.

G. E. Perlin and K. D. Wise, "The effect of the substrate on the extracellular neural activity recorded with micromachined silicon microprobes," in Dig. IEEE Conf. Eng. Med. Biol., San Francisco, CA, Sep. 2004:2002-2005.

J. Ji, and K. D. Wise, "An implantable CMOS circuit interface for multiplexed microelectrode recording arrays," IEEE J. Solid-State Circuits. 1992. vol. 27 (No. 3):433-443.

B. Frazier, D. P. O'Brien and M. G. Allen, "Two dimensional metallic microelectrode arrays for extracellular stimulation and recording of neurons," in 1993 IEEE Micro Electro Mechanical Systems Conf., Fort Lauderdale, FL, Feb. 7-10:195-200.

Q. Bai and K. D. Wise, "A high-yield microassembly structure for three-dimensional microelectrode arrays" IEEE Trans. Biomed. Eng., 2000. vol. 47 (No. 3):281-289.

A. Robinson, "The electrical properties of metal microelectrodes", Proc. IEEE, 1968. vol. 56 (No. 6):1065-1071.

Y. Yao, M. N. Gulari, J. F. Hetke, and K. D. Wise, "A self-testing multiplexed CMOS Stimulating Probe for a 1024-site neural prosthesis", in Transducers '03: The 12th Internatianal Conference on Solid State Sensors, Anuators and Microsystems. Boston, MA, Jun. 8-12, 2003:1213-1216.

G.E. Perlin, A. M. Sodagar, and K. D. Wise, "Neural recording front-end designs for fully implantable neuroscience applications and neural prosthetic microsystems," in IEEE Int. Conf. Eng. Med. Biol., New York, Sep. 2006: 2982-2985.

G. A. May, S. A. Shamma, and R. L. White, "A tantalum-on-sapphire microelectrode array," IEEE Trans. Electron Devices. 1979. vol. ED-26 (No. 12):1932-1939.

O. J. Prohaska et al., "Thin-film multiple electrode probes: Possibilities and limitations," IEEE Trans. Biomed. Eng. 1986. vol. BME-33 (No. 2):223-229.

N. A. Blum et al., "Multisite microprobes for neural recordings", IEEE Trans. Biomed. Eng. 1991. vol. 38 (No. 1):68-74.

S. A. Boppart et al., "A Flexible Perforated Microelectrode Array for Extended Neural Recordings", IEEE Trans. Biomed. Eng. 1992. vol. 39 (No. 1):37-42.

K. Lee et al.,"Polyimide based neural implants with stiffness improvement", Sensors and Actuators B, 2004. vol. 102:67-72.

L. Frewin et al., "Atomic Force Microscopy Analysis of Central Nervous System Cell Morphology on Silicon Carbide and Diamond Substrates", Journal of Molecular Recognition, 2009. vol. 22: 380-388.

Coletti, M. et al.,"Biocompatibility and wettability of crystalline SiC and Si surfaces", in 29th Annual IEEE EMBS Proceedings, Aug. 23-26, 2007: 5849-5852.

R. Yakimova et al., "Surface functionalization and biomedical applications based on SiC", J. Phys. D: Appl. Phys., 2007. vol. 40:6435-6442.

U. Kalnins et al., Clinical outcomes of silicon carbide coated stents in patient with coronary disease. Med. Sci. Monit., 2002. vol. 8 (No. 2):16-20.

X. Li et al., "Micro/Nanoscale Mechanical and Tribological Characterization of SiC for Orthopedic Applications", J Biomed Mater Res B Appl Biomater, 2005. vol. 72 (No. 2):353-361.

J-M. Hsua et al., "Characterization of a-SiCx:H thin films as an encapsulation material for integrated silicon based neural interface devices" Thin Solid Films, 2007. vol. 516 (No. 1):34-41.

Jackson and E. E. Fetz, "Compact movable microwire array for long-term chronic unit recording in cerebral cortex of primates", J. Neurophysiol., 2007. vol. 98:3109-3118.

V. S. Polikov et al., "Response of brain tissue to chronically implanted neural electrodes", J. of Neuroscience Methods, 2005. vol. 148:1-18.

J. C. Williams et al., "Stability of chronic multichannel neural recordings: implications for a long-term neural interface", Neurocomputing, 1999. vol. 26-27: 1069-1076.

J. C. Williams et al., "Long-term neural recording characteristics of wire microelectrode arrays implanted in cerebral cortex" Brain Res Protoc, 1999. vol. 4:303-313.

L. Hodgkin and A. F. Huxley, "The components of membrane conductance in the giant axon of Loligo", J. Physiol (Lond.), 1952. vol. 116 (No. 4):473-496.

S. Bjornsson et al., "Effects of insertion conditions on tissue strain and vascular damage during neuroprosthetic device insertion", J. Neural Eng., 2006. vol. 3:196-207.

KV Emtsev et al., Towards wafer-size graphene layers by atmospheric pressure graphitization of silicon carbide. Nature Materials. 2009. vol. 8:203-207.

F. Williams, "On the mechanisms of biocompatibility," Biomaterials, 2008. vol. 29:2941-53.

K. K. Lee et al., "Polyimide based intracortical neural implant with improved structural stiffness" J Micromech Microeng, 2004. vol. 14:32-37.

Frewin C. L., The Neuron-SiC Interface: Biocompatibility Study and BMI Device Development. Graduate School Theses and Dissertations. Paper 1973. May 28, 2009. (http://scholarcommons.usf.edu./edt/1973).

M. Chardack, et al., "Correction of Complete Heart Block by a Transistorized, Self-Contained, and Implantable Pacemaker," Circulation, vol. 22, pp. 732-732, 1960.

(56) References Cited

OTHER PUBLICATIONS

International Search Report for PCT/US2001/058376 (filing date of Nov. 30, 2010) with a mailing date of Aug. 19, 2011, Applicant: University of South Florida et al.
Preliminary Report of Patentability for PCT/US2010/058376 (filing date of Nov. 30, 2010) with a mailing date of Jun. 14, 2012, Applicant: University of South Florida et al.
International Search Report for PCT/US2011/062601 (filing date of Nov. 30, 2011) with a mailing date of Jul. 31, 2012, Applicant: University of South Florida et al.
Preliminary Report of Patentability for PCT/US2011/062601 (filing date of Nov. 30, 2011) with a mailing date of Jun. 13, 2013, Applicant: University of South Florida et al.

\* cited by examiner

GRAPHENE ELECTRODES ON A PLANAR CUBIC SILICON CARBIDE (3C-SIC) LONG TERM IMPLANTABLE NEURONAL PROSTHETIC DEVICE

CROSS REFERENCE TO RELATED APPLICATIONS

This application is a continuation of and claims priority to prior filed International Application, serial Number PCT/US2011/062601 filed Nov. 30, 2011, which is a non-provisional of U.S. Provisional Patent Application 61/418,200, filed Nov. 30, 2010, by the same inventors, each of which is incorporated herein by reference.

FIELD OF THE INVENTION

This invention relates to the field of medical devices. More specifically, it relates to an implantable neuronal prosthetic and method of manufacture thereof having biocompatible graphene electrodes.

BACKGROUND OF INVENTION

One of the problems with long term, implantable biomedical devices arises from the response of the body to one or more of the materials that are used to construct the device, or the degradation of the material due to the body environment. This problem has led to advances in the materials used for mechanical devices that replace bones, joints, and teeth, as well as coronary devices such as arterial stents or artificial heart valves. Biomedical devices gained an entirely new level of complexity with the advent of the microchip which adds electrical interaction with the cells to the previously utilized mechanical interaction. Unfortunately, direct long-term interaction for the microchip with the body is difficult as most of the materials used in microchips are either chemically reactive, toxic, or both, and must be hermetically sealed to maintain a degree of biocompatibility. This separation between the electrical elements of the biomedical device requires use of a transducer, an object which transforms the interaction between the body and a specific material, the analyte, into another signal which can interact with electronics. One popular transducer for both biosensors and electrical stimulation devices is the utilization of an extremely conductive material, otherwise known as an electrode.

Like every other material utilized in long term implantation, electrodes must be made of a non-corrosive, highly conductive material that does not cause adverse body reactions, is thromboresistant, and has good material durability and strength. Noble metals like gold, platinum, and iridium have been traditionally used in many electrically-active biomedical devices. Transmission electrodes that activate action potentials in electrically active cells, like the ones used in implantable heart pacemakers, have longevity in vivo, but these same electrodes experience many problems when miniaturized for smaller microelectrode array devices. This problem is most exemplified by the generation of Faradaic reactions at the surface of the electrode that produce harmful reactive species which interact with tissue near the electrode and lead to an inflammatory response. Faradic reactions are generated either due to the electrochemical interaction between the electrode and the electrolyte, but can also be dependent on the large charge injections required for cellular membrane depolarization which pass through a small geometrical surface area (i.e., high current density). The ideal electrode would not produce Faradaic reactions and have a large geometrical surface area to allow for large charge injection.

An example is the brain machine interface (BMI), which offers therapeutic options to relieve many individuals suffering from central nervous system (CNS) or peripheral nervous system (PNS) disabilities due to disease or trauma. The central component of the BMI system is the neuronal prosthetic which interacts with the body's electrophysiological signals. Implantable neuronal prosthetics have the ability to not only receive electrical signals directly from neurons or muscles, but they can deliver electrical signals to these same cells and provide a means for a closed loop BMI systems. These devices are unfortunately still regulated to experimental BMI systems due to a severe long term in vivo reliability issue. Device failure over time is thought to arise from lowered material biocompatibility which activates the immune response of the body, or failure can arise due to deterioration of the electrical interaction point due to Faradaic reactions caused by the high current densities needed for neuron action potential activation. The solution to this problem is to find materials that are physically and chemically resilient, biocompatible, and have great electrical properties.

Graphene is a two-dimensional (2D) monoatomic layer of graphite which has shown exceptional mechanical, optical, and electrical properties enabling it to perform a wide range of different applications. It is the basic building block for many popular carbon containing materials like the 0D "Bucky ball" C60, the popular 1D carbon nanotube, and if layered into a 3D structure, it becomes common graphite. Graphene was originally obtained via mechanical exfoliation of graphite, the so-called 'scotch tape method', which however yields graphene flakes of limited sizes. Many different methodologies like sheet extraction from graphene dispersions to epitaxial growth on semiconductors, silicon dioxide, and metals have been used to gain large area sheets of graphene. One interesting method utilizes the sublimation of silicon (Si) from the surface of silicon carbide (SiC), which has generated large scale monolayer and few-layer epitaxial graphene sheets.

Although graphene is an attractive material for the study of quantum electrodynamics, it presents an equal attraction for the generation of a new set of electronic and mechanical devices superior to Si.

SUMMARY OF INVENTION

Graphene is utilized as the electrode contacts on the implantable neuronal prosthetic due to this material's chemical resilience, extended surface area over conventionally used electrode materials, excellent electrical conductivity and specific capacitance in electrolytes, and biocompatibility. Graphene is naturally formed through the thermal decomposition of the surface of silicon carbide, thereby making this an ideal material combination. It also has the ability to be fashioned into device structures using common lithography and oxygen plasma etching.

BRIEF DESCRIPTION OF THE DRAWINGS

For a fuller understanding of the invention, reference should be made to the following detailed description, taken in connection with the accompanying drawings, in which:

FIG. 1 is an illustration of the general process for the generation of a planar 3C—SiC based graphene electrode neural prosthetic system with electrodes located on a single side of the shank.

FIG. 2 is an illustration of the general process steps for the generation of a planar 3C—SiC based graphene electrode neural prosthetic system with electrodes on both faces of the planar system. The steps outlined in FIGS. 2(A)-2(H) are performed exactly as detailed for the one sided shank contacting device. After the generation of the graphene electrodes on the surface of the 3C—SiC epitaxial film, FIGS. 2(I and J) show that a thin coat of photoresist is applied and the front side of the wafer is temporarily bonded to a Si wafer to provide mechanical support for further processing. The silicon substrate is removed using wet or dry chemical etching, which results in a freestanding 3C—SiC structure. Deep reactive ion etching (DRIE) of about 6 micros of silicon carbide of the 3C—SiC interface surface will remove damage formed during epitaxial growth from either the lattice mismatch or Si evaporation voids. The graphene is then formed on the 3C—SiC surface as outlined above and patterned using lithography and O2 plasma etching. Interfacial defects caused by the lattice mismatch between Si and SiC as well as Si evaporation are reduced through etching back the 3C—SiC backside surface. 3C—SiC interface defects are mainly generated through heteroepitaxial growth due to thermal coefficient and lattice mismatch, but are also due to atomic layer stacking faults and twining. It is well known that many of these defects annihilate themselves as the crystal grows in thickness. The damage can be eliminated through this etch so as to make the final product more structurally and electrically sound. FIGS. 2(K and L) show that graphene electrodes are created on the backside of the device through plasma degeneration. FIGS. 2(M and N) indicate that the backside electrodes are isolated by applying insulating amorphous, polycrystalline, or single crystal 3C—SiC on top of the shanks prior to graphene formation, and following lithography and DRIE processing to etch open windows over the electrode ends. Next, the Si handle wafer is removed, the front side is coated in the same insulating SiC material, and windows are opened over the electrodes as shown in FIGS. 2(O and P). FIGS. 2(Q and R) show that the shanks are patterned using photoresist and subsequent etching of the unwanted material between the shanks, leaving freestanding neuronal prosthetic electrodes. FIGS. 2(S and T) show the final neuronal prosthetic device.

FIG. 3 is an illustration of (a) ARPES, (b) XPS and (c) AFM characterization of a typical monolayer graphene sample used in the invention.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The present invention provides a long term implantable neuronal prosthetic device including graphene electrodes on a planar 3C—SiC. Graphene is mechanically and chemically resilient. Single layer graphene has excellent conduction properties due to its zero band-gap and large, uniform sheets are ideal for the production of multiple, large scale uniform electrodes. Additionally, the band-gap of graphene can be tuned using the underlying substrate, the addition of multiple graphitic layers, and even the geometry of the devices. Graphene performs superiorly as an electrochemical double layer capacitive electrode, displaying specific capacitances of 135 and 99 F/g in aqueous and organic electrolytes. With a surface area of 2630 m2g−1, graphene has double the surface area of carbon nanotubes and 200 times that of graphite, therefore reducing the chance of electrochemical reaction and subsequent damage from capacitive charge transfer to an irreversible Faradaic reaction because of small geometric area to charge transfer relationship.

Graphene has shown markers of biocompatibility. Graphene obtained from the decomposition of SiC allows access to all of these previously mentioned features as well as widening the number of options in device construction with the addition of the powerful semiconductor. Compared with other conventional electrodes, graphene electrodes have the ability to produce the appropriate threshold charge densities required for neuron and muscle stimulation.

In one embodiment, the method of manufacture of graphene electrodes on a single side of a planar 3C—SiC implantable neuronal prosthetic is shown in FIG. 1(A)-1(H). The process begins with heteroepitaxially growing 3C—SiC 120 on a cubic lattice crystalline substrate 110, like silicon, to a thickness of 15 to 20 µm, as shown in FIGS. 1(A-D). FIGS. 1(E and F) show that graphene 130 can be generated on the surface of the 3C—SiC 120 using thermal decomposition of the 3C—SiC 120 surface which is possible on any crystalline orientation of 3C—SiC through thermal annealing in Ar ambient gas and temperatures greater than 1000° C. (V. Y. Aristov, et al., "Graphene Synthesis on Cubic SiC/Si Wafers. Perspectives for Mass Production of Graphene-Based Electronic Devices," Nano Letters, 10, (2010) 992-995). Common lithographic techniques, such as, but not limited to the utilization of ultraviolet or electron beam exposure of photoresist are used to pattern electrodes 140 on the graphene, and an O2 plasma will etch any exposed graphene as shown in FIGS. 1(G and H). The electrodes 140 can be smaller than conventional electrodes due to the larger electrolytic specific capacitance of graphene as well as a greater surface area, allowing for less invasive shanks and more electrodes per shank resulting in higher connectivity to the neurons in the brain. The surface of the graphene/3C—SiC layer is coated in highly insulating amorphous, polycrystalline, or single crystal 3C—SiC 150 and lithography is used to open windows over the electrode ends, as exemplified in FIGS. 1(I and J). The substrate wafer 110 is removed from the backside of the device using wet or dry etching techniques. Figures (K and L) show the open windows over the freestanding electronic device. A final mask for the physical shank assembly, as shown in FIGS. 1(M and N), is used to mold the final device shown in FIGS. 1(O and P). In this embodiment, a single sided, planar shank contacts in planar neuronal prosthetics is produced.

Figure 1A:
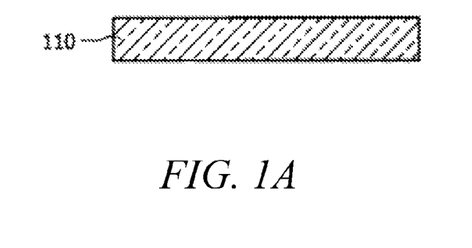
FIGS. 1A-1D show the process beginning with heteroepitaxially growing 3C—SiC on a cubic lattice crystalline substrate such as silicon to a thickness of about 15 to 20 µm.
Figure 1B:
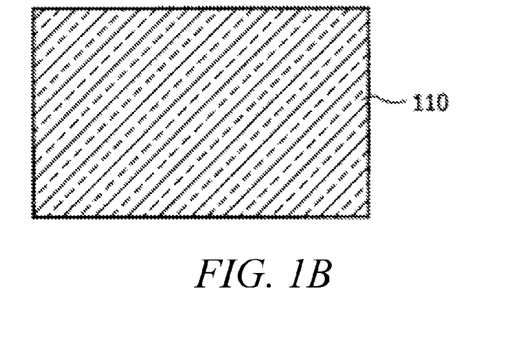
Figure 1C:
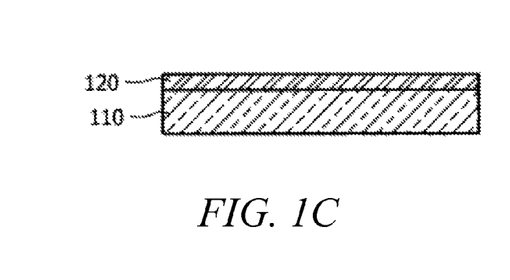
Figure 1D:
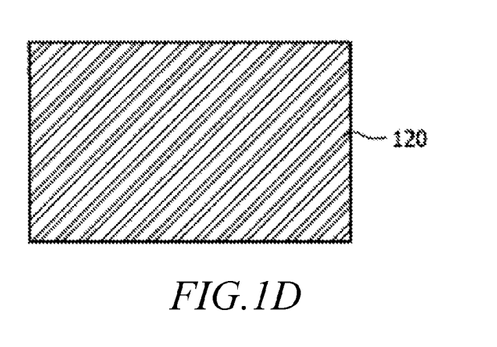
Figure 1E:
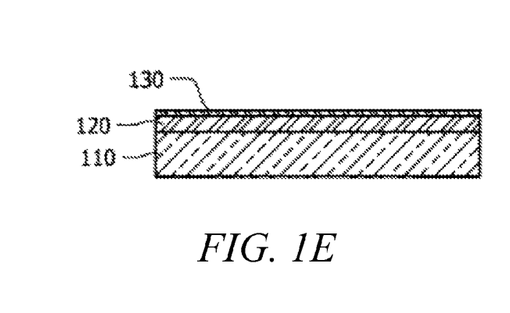
FIGS. 1E and F show that graphene can be generated on the surface of the 3C—SiC using thermal decomposition of the 3C—SiC surface which is possible on any crystalline orientation of 3C—SiC through thermal annealing in Ar ambient gas and temperatures greater than 1000° C. Common lithographic techniques, such as, but not limited to the utilization of ultraviolet or electron beam exposure of photoresist are used to pattern electrodes on the graphene, and an O2 plasma will etch any exposed graphene as shown in FIGS. 1G and H. The surface of the graphene/3C—SiC layer is coated in highly insulating amorphous, polycrystalline, or single crystal 3C—SiC and lithography is used to open windows over the electrode ends, as exemplified in FIGS. 1I and J. The substrate wafer is removed from the backside of the device using wet or dry etching techniques.
Figure 1F:
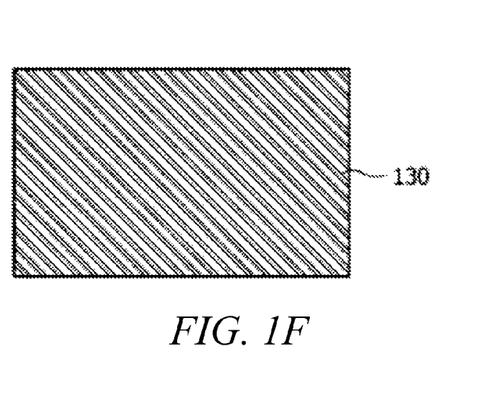
Figure 1G:
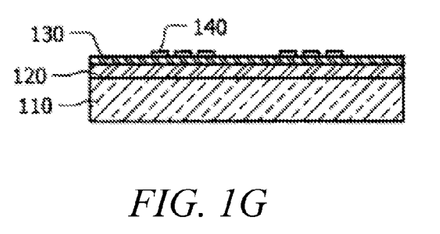
Figure 1H:
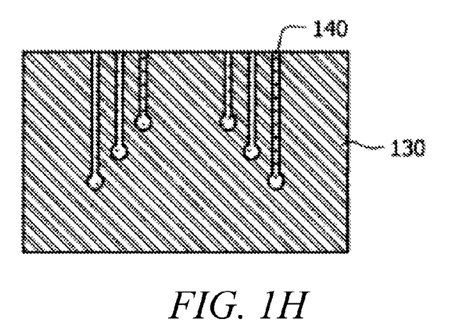
Figure 1I:
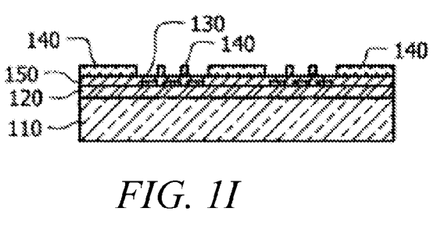
Figure 1J:
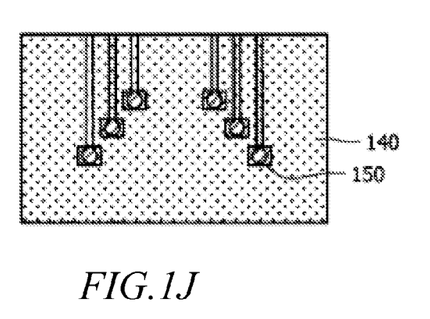
Figure 1K:
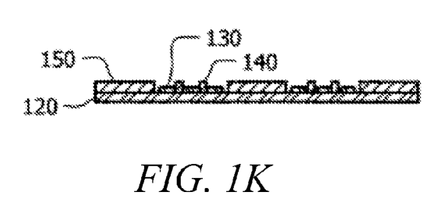
FIGS. 1K and L show the open windows over the freestanding electronic device. A final mask for the physical shank assembly, as shown in FIGS. 1M and N, is used to mold the final device shown in FIGS. 1O and P which is a single sided, planar shank for use in planar neuronal prosthetics.
Figure 1L:
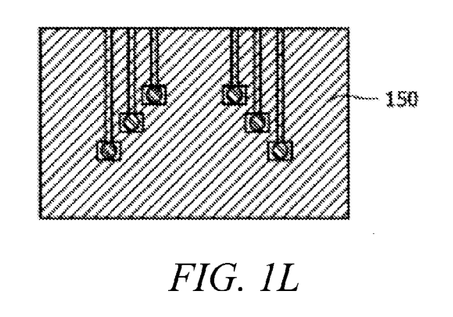
Figure 1M:
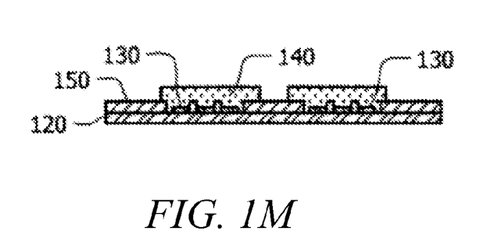
Figure 1N:
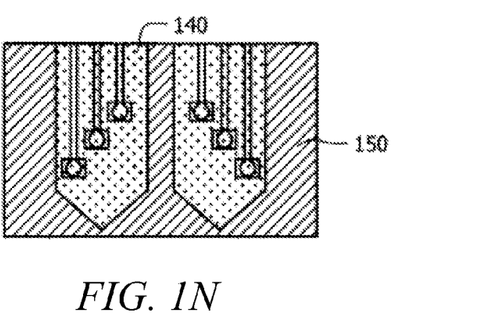
Figures 1O, 1P:
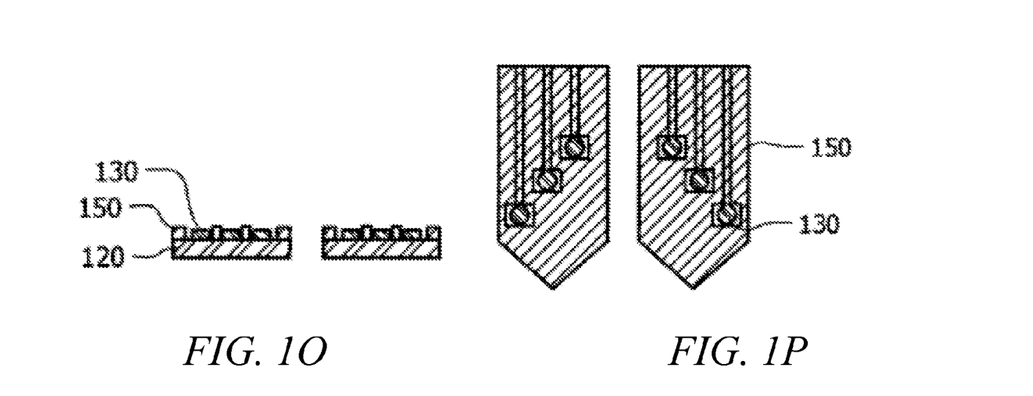
Figure 2A:
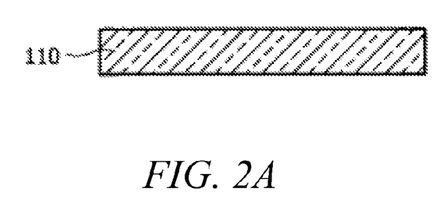
Figure 2B:
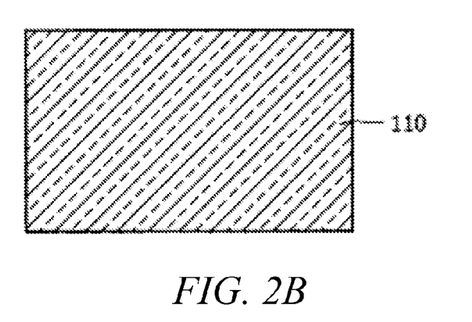
Figure 2C:
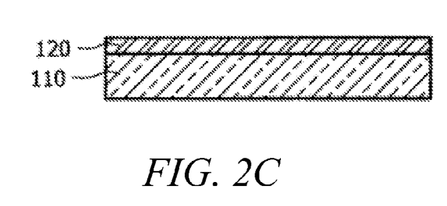
Figure 2D:
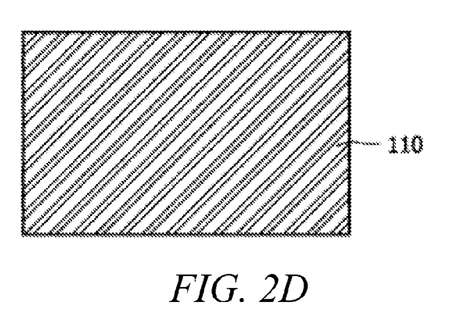
Figure 2E:
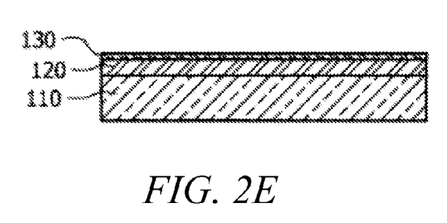
Figure 2F:
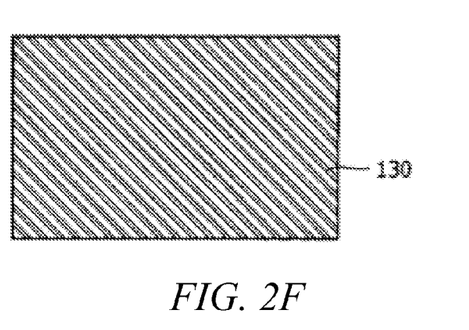
Figure 2G:
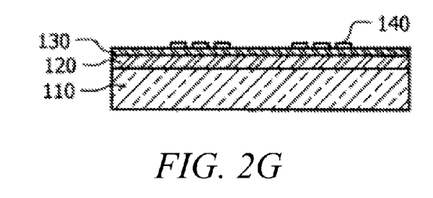
Figure 2H:
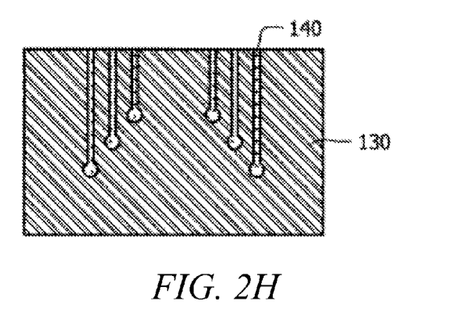
Figure 2I:
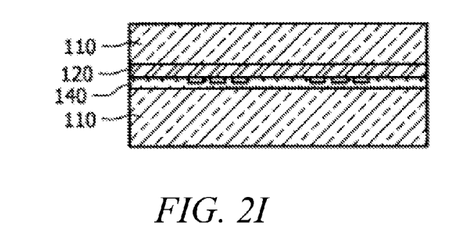
Figure 2J:
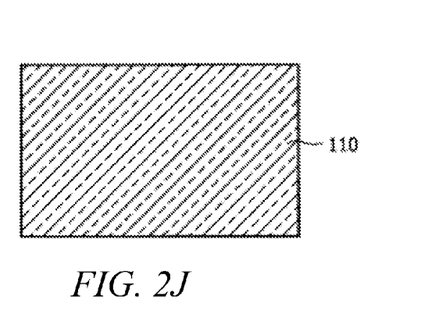
Figure 2K:
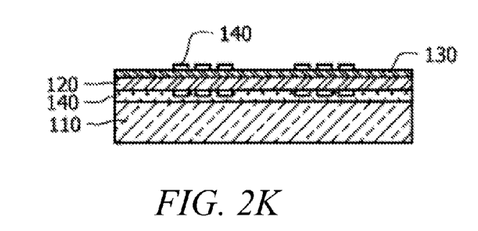
Figure 2L:
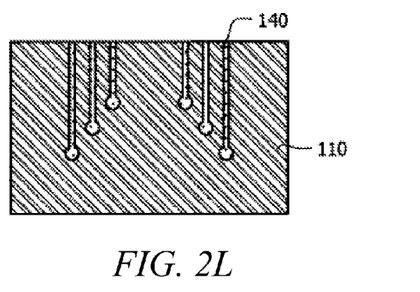
Figure 2M:
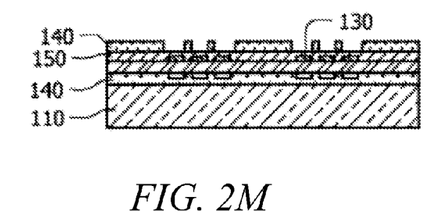
Figure 2N:
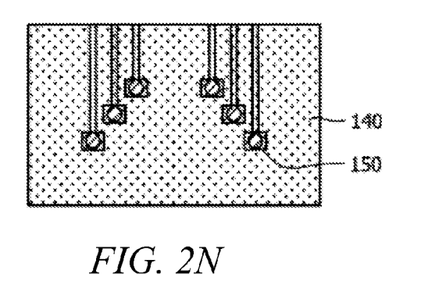
Figure 2O:
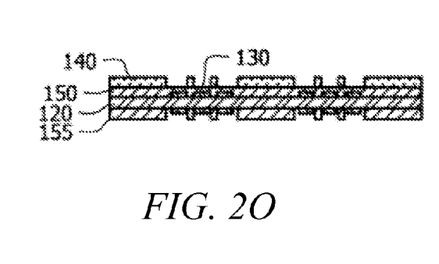
Figure 2P:
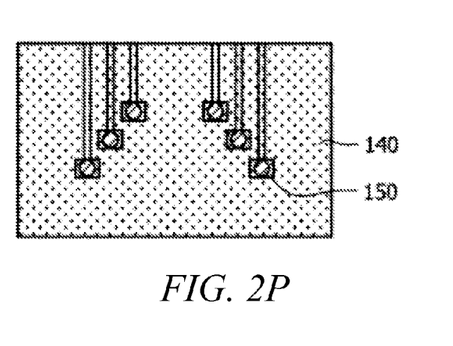
Figure 2Q:
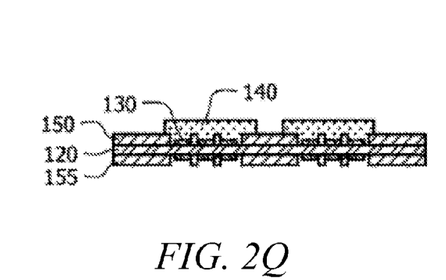
Figure 2R:
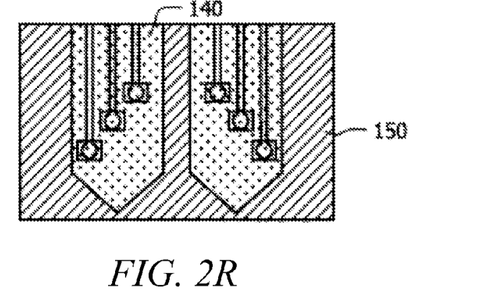
Figure 2S:
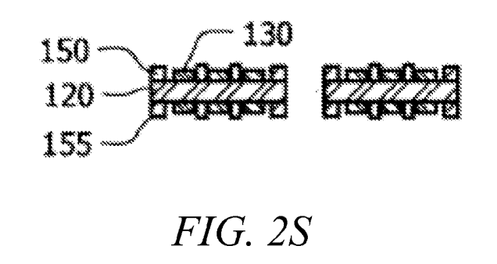
Figure 2T:
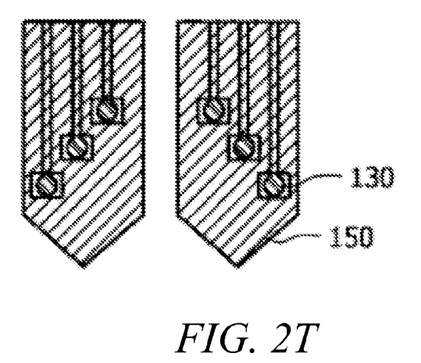

In an alternative embodiment, the method of manufacture of graphene electrodes on a two-sided planar 3C—SiC implantable neuronal prosthetic is shown in FIGS. 2(A)-2(T). The steps outlined in FIGS. 2(A)-2(H) are performed exactly as detailed above for the one sided shank contacting device. After the generation of the graphene electrodes 140 on the surface of the 3C—SiC epitaxial film 120, FIGS. 2(I and J) show that a thin coat of photoresist is applied and the front side of the wafer 110 is temporarily bonded to a Si wafer 110 to provide mechanical support for further processing. The silicon substrate 110 is removed using wet or dry chemical etching, which results in a freestanding 3C—SiC structure. Deep reactive ion etching (DRIE) of about 6 micros of silicon carbide of the 3C—SiC interface surface will remove damage formed during epitaxial growth from either the lattice mismatch or Si evaporation voids. The graphene 130 is then formed on the 3C—SiC surface 120 as outlined above and patterned using lithography and O2 plasma etching. Interfacial defects caused by the lattice mismatch between Si and SiC as well as Si evaporation are reduced through etching back the 3C—SiC backside surface. 3C—SiC interface defects are mainly generated through heteroepitaxial growth due to thermal coefficient and lattice mismatch, but are also due to atomic layer stacking faults and twining. It is well known that many of these defects annihilate themselves as the crystal grows in thickness. The damage can be eliminated through this etch so as to make the final product more structurally and electrically sound. FIGS. 2(K and L) show that graphene electrodes 140 are created on the backside of the device through plasma degeneration. FIGS. 2(M and N) indicate that the backside electrodes are isolated by applying insulating amorphous, polycrystalline, or single crystal 3C—SiC 150 on top of the shanks prior to graphene formation, and following lithography and DRIE processing to etch open windows over the electrode ends. Next, the Si handle wafer is removed, the front side is coated in the same insulating SiC material 155, and windows are opened over the electrodes as shown in FIGS. 2(O and P). FIGS. 2(Q and R) show that the shanks are patterned using photoresist and subsequent etching of the unwanted material between the shanks, leaving freestanding neuronal prosthetic electrodes. FIGS. 2(S and T) show the final neuronal prosthetic device.

The completed shank devices are attached to electronics to facilitate signal transmission and recording. A fully-implantable device would require electronics for conditioning and amplifying received signals via amplifiers, filters, etc.; signal generation to excite an action potential from neurons or muscles (transmission); and a control system to manage the signals, wireless communication, and finally power management. Power for the device can be delivered with rechargeable batteries and/or inductive generation. Although electronics can be generated in 3C—SiC, they can more easily be realized in Si. The latter method implies that Si electronics are realized separately and then attached (both electrically and physically) to the 3C—SiC device structure through standard semiconductor die bonding techniques. The vulnerable Si electronics are then hermetically sealed with a chemically resistive, biocompatible material, like amorphous silicon carbide, to protect it from attacks by the body's immune system. An alternative method to facilitate the onboard electronics requires that a part of the Si substrate upon which the 3C—SiC was grown is preserved for electronics implementation. The required electronics are realized in the preserved silicon tab portion of the shanks and connected to the 3C—SiC and graphene through interconnections made using standard microelectronic processing (metal traces, insulation, conductive via connections, etc.). Either final device, consisting of signal and power electronics and at least one implantable shank with at least one electrode, can be used as the main interface component of a brain machine interface (BMI) device.

Biocompatability of Graphene on SiC

The interaction of HaCaT (human keratinocyte) cells on epitaxial graphene was compared with that of bare 6H—SiC (0001) while using polystyrene (PSt) as the control surface. Fluorescent optical microscopy and MTT [3-(4,5-dimethylthiazol-2-yl)-2,5-diphenyltetrazolium bromide] assays were used to assess the biocompatibility of these surfaces.

Cell viability and cell morphology of these surfaces was compared. Two different cleaning procedures were employed on the graphene surfaces tested. The optical inspection results after 72 hours of cell incubation showed that the ethanol sterilization step is required in order to have a more homogeneous and enhanced cell adhesion on graphene surfaces.

The graphene films were epitaxially grown on 6H—SiC (0001) substrates. Initially, the 6H—SiC samples were H2 etched in order to remove any commercial polishing damage and to obtain a well ordered surface. Subsequently, graphitization was performed under an Ar environment at annealing temperature between 1600 and 1700° C. (K V Emtsev, A Bostwick, K Horn, et al. Nature Materials 8 (2009) 203-207). The quality and thickness of the graphene films were evaluated by angle-resolved photoemission spectroscopy (ARPES) and X-ray photoelectron spectroscopy (XPS). AFM and surface water contact angle (SWCA) were used to assess the surface morphology and wettability of SiC and graphene. The surface topography analysis was done using an XE-100 Advanced Scanning Microscope from Park Systems. The SWCA data were obtained from the average of three 10 µl droplets deposited on different areas of the sample. The images of the liquid droplets were obtained using a KSV CAM101 system from KSV Instruments and the contact angle (A) was estimated by measuring the angles between the baseline of the droplet and the tangent at the droplet boundary.

Prior to cell seeding the graphene surfaces were cleaned of possible air contamination by performing thermal annealing under an Ar atmosphere at 700° C. in a chemical vapor deposition (CVD) reactor. While for one set of samples (A) cell seeding was performed without any further surface treatment, for another set of samples (B) an additional sterilization step via immersion in ethanol was performed. The different surface treatment methods were considered for graphene with the intention of learning if the final ethanol dip (typically used to prevent bacteria formation prior to cell seeding) would change the cell morphology and proliferation. The 6H—SiC surfaces were first HF dipped to remove the native oxide, then annealed as with the graphene samples in Ar atmosphere at 700° C. and finally ethanol dipped.

For the cell morphology analysis and viability assays, the HaCaT cells were counted and plated on the PSt controls, 6H—SiC and epitaxial graphene samples at a density of 30,000 cells/cm$^2$ in Dulbecco's Modified Eagle's Medium (DMEM) supplemented with 10% FBS and incubated for 72 hours. In addition cell morphology inspection analysis was performed after 120 hours on extra samples from group B and on 6H—SiC. A 5 µM solution of CMFDA (5-chloromethylfluoresceindiacetate) cell tracker dye was used to perform the cell morphology analysis via fluorescent microscopy.

Figure 3A:
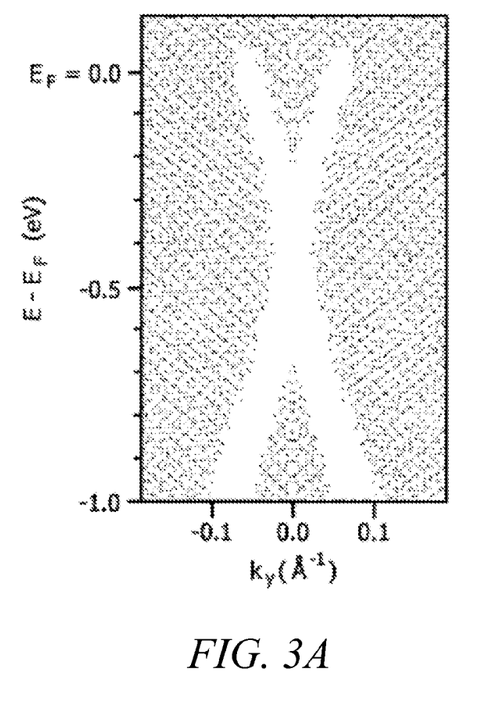
FIG. 3(a) Dispersion of the π-bands measured with UV excited ARPES (hv=40.8 eV) with a display analyzer oriented for momentum scans perpendicular to the ΓK-direction of the graphene Brillouin zone.

Characterization of both the epitaxial graphene and 6H—SiC surfaces was performed to assess the surface properties prior to cell seeding. FIG. 3a shows the dispersion of the π-bands around the K-point of the graphene Brillouin zone measured via ARPES.

Figure 3B:
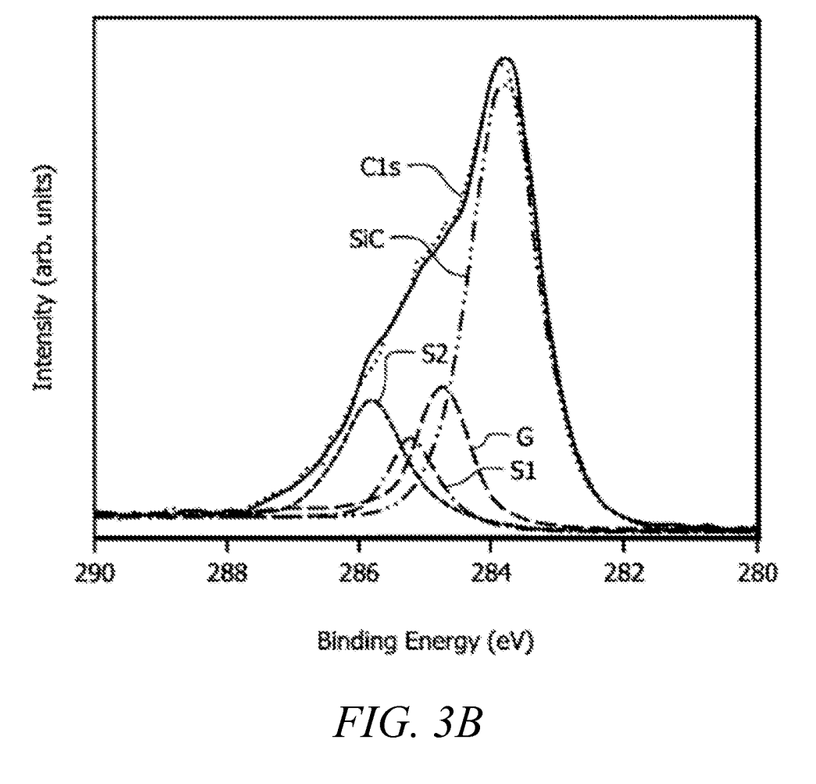
FIG. 3(b) C1s XPS spectrum measured using a non-monochromatic Mg Kα source, hv=1253.6 eV, plotted as a black line and fitted components.
Figure 3C:
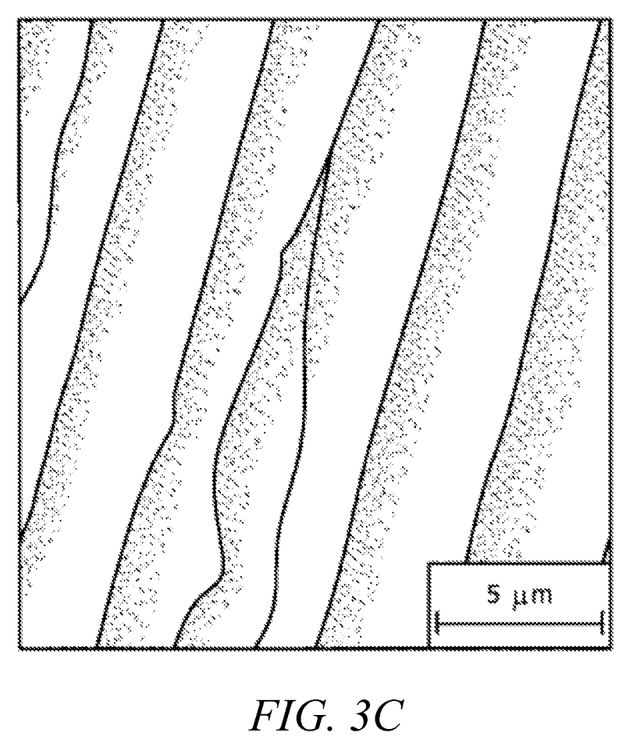
FIG. 3(c) AFM micrograph of epitaxial graphene on 6H—SiC (0001). Scan area 20 µm×20 µm. Scale −10 nm to 8 nm.
Figure 4A:
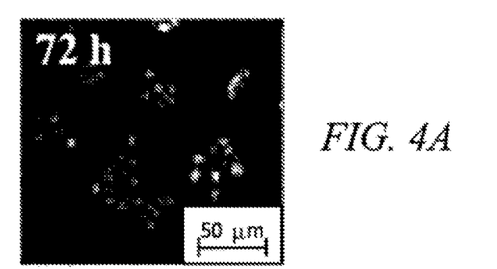
FIG. 4 is a depiction of fluorescent micrographs of HaCaTs after 72 hour on a) graphene (A), b) graphene (B), c) 6H—SiC (0001), and after 120 hrs on d) 6H—SiC(0001) and e) graphene (B).
Figure 4B:
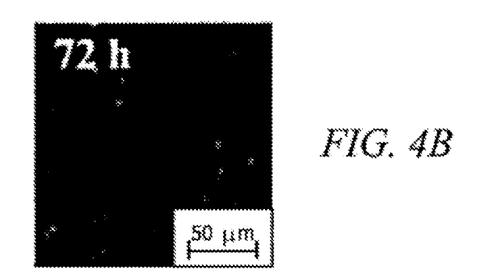
Figure 4C:
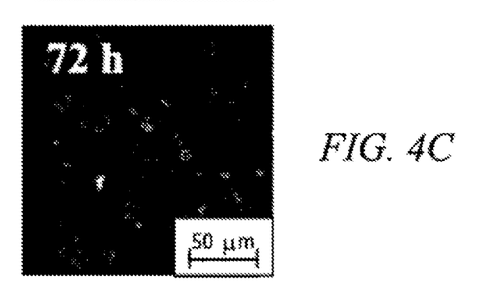
Figure 4D:
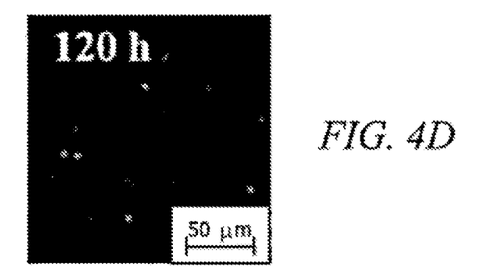
Figure 4E:
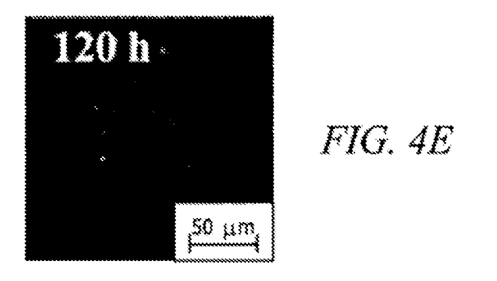

The π-bands linear dispersion and the displacement of the Fermi level above the Dirac point of circa 0.42 eV are characteristic features of monolayer graphene epitaxially grown on SiC(0001). Also the C1s XPS spectrum shown in FIG. 3b confirms the monolayer nature of the adopted graphene films. The analysis of the graphene surface topography with AFM (FIG. 3c) showed indication of large continuous terraces, on average 3.6±2 µm long with a step height of 6.3±3.6 nm, which is larger than the original H2 etched 6H—SiC substrate terraces.

The SWCA measured for graphene cleaned by methods A and B were 87.3°±9.5° and 94.9°±3.2°, respectively. These results confirm the well-known hydrophobicity of graphene and demonstrate that the sterilization in ethanol did not change the affinity of the surface to water in a statistically significant way. For 6H—SiC the SWCAs was 47° 0.2±3°, hereby confirming the hydrophilic character of the surface even though partially reduced with respect to what was reported in C Coletti, M Jaroszeski, A. Pallaoro, A M Hoff, S Iannotta and S E Saddow, IEEE EMBS proc. (2007), 5850-5853 (i.e., SWCA ~25° for a Piranha and hydrofluoric acid (HF) treated 6H—SiC(0001) surface) by the thermal annealing step.

FIG. 4 shows after 72 hours, for both graphene and 6H—SiC, the morphology of the HaCaT cells was similar to that on the PSt control with signs of cell-cell interaction and cell-substrate interaction. For the graphene substrates from group A, as seen in FIG. 4a, small islands of cells were observed compared to the monolayer that started forming on the graphene surface cleaned by method B shown in FIG. 4b. The 6H—SiC samples also showed via optical inspection clear signs of an initial formation of a cell monolayer (FIG. 4c). It is apparent from the comparison of FIGS. 4a and 4b that the ethanol dip step favors a more homogeneous cell adhesion and for this reason subsequent experiments whose results are reported below were performed only on samples cleaned by using method B.

HaCaTs tend to form groups of cells such as islands, and with time they start growing tighter and closer to each other and eventually form a conformal layer of cells. Consequently at a time of 120 hours optical inspection of cells plated graphene and 6H—SiC samples was performed with the intent of checking whether the cells would grow to confluence. The 120 hrs optical inspection data showed a homogeneous monolayer of cells formed on both graphene and 6H—SiC, shown in FIGS. 4d and 4e.

The MTT assays provided an average value of cell viability after 72 hrs of incubation and with respect to the PSt control.

The results were 17±0.07 (std deviation of the mean) for graphene and 58±0.05 for 6H—SiC. After 120 hrs of incubation, the formation of a cell monolayer on graphene substrates in a similar to 6H—SiC, as shown in FIGS. 2d and 2e.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

What is claimed is:

1. An implantable neuronal prosthetic device for placement in a patient for receiving and sending electrical signals, comprising:
   at least one electrode shank adapted for arrangement in said patient having at least one graphene electrode contact disposed on its surface and arranged to electrically couple with said patient, said at least one electrode shank being formed on a single crystal cubic silicon carbide.

2. An implantable neuronal prosthetic device for receiving and sending electrical signals as in claim 1, further comprising an insulation layer of amorphous, polycrystalline, or single crystal silicon carbide disposed over said electrode shank, said insulation layer of amorphous, polycrystalline, or single crystal silicon carbide being removed from said graphene electrode contact.

3. An implantable neuronal prosthetic device for receiving and sending electrical signals as in claim 1, wherein the graphene electrode is deposited on one side of the electrode shank.

4. An implantable neuronal prosthetic device for receiving and sending electrical signals as in claim 1, wherein the graphene electrode is deposited on two sides of the electrode shank.

5. An implantable neuronal prosthetic device for receiving and sending electrical signals as in claim 1, further comprising signal control electronics attached to said at least one electrode shank and in communication with said at least one grapheme electrode contact.

6. An implantable neuronal prosthetic device for receiving and sending electrical signals as in claim 1, further comprising a plurality of said at least one electrode shanks being arranged into a matrix.

7. A method of manufacturing an implantable neuronal prosthetic device for placement in a patient for receiving and sending electrical signals, comprising the steps of:
   forming at least one electrode shank adapted for arrangement in said patient out of a single crystal cubic silicon carbide;
   forming a layer of graphene sheet on a surface of at least one electrode shank; and
   patterning the layer of graphene sheet to at least one graphene electrode contact, said at least one electrode being arranged to electrically couple with said patient.

8. The method of claim 7, wherein the at least one electrode shank is formed by heteroepitaxially growing the crystal cubic silicon carbide on a cubic lattice crystalline substrate wafer.

9. The method of claim 8, wherein the silicon carbide is grown on one side of cubic lattice crystalline substrate wafer, and further comprising removing the substrate wafer from the other side of the substrate wafer.

10. The method of claim 9, wherein removing substrate wafer is achieved by using wet or dry etching techniques.

11. The method of claim 8, wherein silicon carbide is grown on both sides of cubic lattice crystalline substrate wafer, and further comprising temporarily bonding the graphene electrode side to a supporting wafer, and cleaning interface defects on the other side.

12. The method of claim 11, wherein cleaning the interface defects is achieved by the reactive ion etching about 6 µm microns of silicon carbide.

13. The method of claim 7, wherein forming the layer of graphene sheet upon the surface is achieved by high-temperature annealing in Ar ambient to realize thermal decomposition of the 3C—SiC surface.

14. The method of claim 7, wherein forming the layer of graphene sheet upon the surface is through ultra high vacuum annealing to decompose the 3C—SiC surface.

15. The method of claim 7, wherein patterning the graphene sheet into electrode contact is through common lithographic techniques and O2 plasma etching.

16. The method of claim 7, wherein at least one graphene electrode contact is formed upon the surface.

17. The method of claim 7, further comprising the steps of:
insulating said at least one electrode shank with amorphous, polycrystalline, or single crystal silicon carbide; and
removing said insulating layer of amorphous, polycrystalline, or single crystal silicon carbide from said at least one graphene electrode contacts such that said at least one electrode contacts are exposed.

18. A method of manufacturing an implantable neuronal prosthetic for placement in a patient for receiving and sending electrical signals as in claim 7, further comprising the step of attaching signal control electronics to said at least one electrode shank, said signal controls electronics being in communication with said at least one electrode contact.

19. A method of manufacturing an implantable neuronal prosthetic for placement in a patient for receiving and sending electrical signals as in claim 7, further comprising the step of arranging a plurality of said at least one electrode shanks into a matrix.

* * * * *